United States Patent [19]

Ramin

[11] Patent Number: 5,725,866
[45] Date of Patent: Mar. 10, 1998

[54] TRANSLUCENT COMPOSITION THAT CAN BE APPLIED TO THE NAIL

[75] Inventor: Roland Ramin, Itteville, France

[73] Assignee: L'Oreal, Paris, France

[21] Appl. No.: 567,099

[22] Filed: Dec. 4, 1995

[30] Foreign Application Priority Data

Dec. 2, 1994 [FR] France .................. 94 14537

[51] Int. Cl.$^6$ .................. A23L 1/30; A61K 7/04; A61K 7/043; A61K 7/42
[52] U.S. Cl. .................. 424/401; 424/59; 252/364; 426/72
[58] Field of Search .................. 424/59, 61, 401; 426/72; 252/364; 524/268; 106/153.1

[56] References Cited

U.S. PATENT DOCUMENTS

| | | | |
|---|---|---|---|
| 3,301,760 | 1/1967 | Jewel | 167/85 |
| 3,954,693 | 5/1976 | Fong | 260/37 N |
| 4,482,538 | 11/1984 | Davies | 424/61 |
| 4,665,116 | 5/1987 | Kornhaber et al. | 524/268 |
| 4,954,619 | 9/1990 | Lang et al. | |

FOREIGN PATENT DOCUMENTS

| | | |
|---|---|---|
| 0300234A2 | 6/1988 | European Pat. Off. |
| 0453628A2 | 10/1990 | European Pat. Off. |
| 0504754A1 | 3/1991 | European Pat. Off. |
| 1453089 | 5/1965 | France |

OTHER PUBLICATIONS

L'Ongle: Griffe Ou Ornement by H. Djelassi, J.J. Berjon, D. Saboureau, D. Heran.

S.T.N. Serreur de bases de donnees, Karlsruhe, DE, Fichier Chemical Abstracts, vol. 117 n. 14251.

Primary Examiner—Thurman K. Page
Assistant Examiner—Sharon Howard
Attorney, Agent, or Firm—Finnegan, Henderson, Farabow, Garrett & Dunner, L.L.P.

[57] ABSTRACT

The invention relates to a composition that can be applied to the nail, that is presented in translucent form, and that comprises at least one film-forming agent, at least one plasticizing agent, at least one solvent, and silica. The composition obtained can be applied properly and in sufficient quantity to the nail and makes it possible to obtain a transparent film with a degree of brilliance.

16 Claims, No Drawings

TRANSLUCENT COMPOSITION THAT CAN BE APPLIED TO THE NAIL

The invention relates to a composition comprising silica that can be applied to natural or synthetic nails and a method of using silica in such a composition. Compositions that can be applied to the nail, of the nail varnish type, generally comprise, as a base, at least one film-forming agent, at least one plasticizer, and at least one solvent.

These compositions are generally very fluid and do not allow proper spreading of the composition on the nail. Indeed, the composition is not deposited on the nail in a sufficient quantity. The addition of at least one compound chosen from clays, such as bentonite, makes it possible to thicken the composition in order to allow better spreading on the nail.

However, the addition of such a compound renders the composition opaque while giving it a more or less yellowish colour, unpleasant to the eye, inside the bottle containing it. This appearance is generally masked by the presence of pigments and/or of colorants in the nail varnish composition.

It is not known to be possible to prepare a composition that can be applied to the nail that is presented in translucent form when it contains a compound such as bentone.

Accordingly, the aim of the invention is to provide a composition that can be applied properly and in sufficient quantity to the nail, that does not opacify, and that is not yellowish in the bottle containing it, while being thixotropic, i.e., capable of passing from a gelled state to a liquid state simply by stirring, and conversely after standing.

One subject of the invention is therefore a composition that can be applied to the nail presented in translucent form, comprising at least one film-forming agent, at least one plasticizing agent, at least one solvent, and pyrogenic silica.

The composition according to the invention has the advantage of making it possible to obtain a transparent film on the nail.

Another advantage of the composition according to the invention is that it is presented in a slightly gelled form, which allows the incorporation of fine insoluble particles which remain in suspension in the medium without significantly modifying the texture and the viscosity of the composition.

A thixotropic and translucent composition can thus be obtained that comprises particles in suspension.

The subject of the invention is also the use of pyrogenic silica as a thickening agent for a translucent composition, optionally as defined above.

The invention relates to a composition that can be applied to the nail, comprising, as a base, at least one film-forming agent, at least one plasticizing agent, and at least one solvent. It comprises, in addition, pyrogenic silica.

The film-forming agent present in the composition according to the invention may be chosen from nitrocellulose or a resin such as an alkyd, acrylic, or polyurethane resin or a resin resulting from the condensation of formaldehyde with an arylsulphonamide.

The film-forming agent may be present in a quantity of 5 to 20%, preferably 10–14%, by weight relative to the total weight of the composition.

The plasticizing agent present in the composition according to the invention may be chosen from camphor, phthalates, and/or esters.

The plasticizing agent may be present in a quantity of 6 to 25%, preferably 16–20%, by weight relative to the total weight of the composition.

The solvent present in the composition according to the invention may be chosen from ethyl, isopropyl or butyl alcohols, or ethyl or butyl acetates, or ketones.

The solvent may be present in a quantity ranging from 60 to 85% by weight, preferably 72–78% by weight, relative to the total weight of the composition.

The composition according to the invention may also comprise at least one diluent which may be chosen from aromatic or aliphatic hydrocarbons such as toluene.

The diluent present in the composition may be present in a quantity ranging from 0 to 35% by weight, preferably 20–27% by weight, relative to the total weight of the composition.

The silica present in the composition according to the invention may be presented in the form of hydrophilic or hydrophobic pyrogenic silica.

The pyrogenic silicas are obtained by high-temperature hydrolysis of a volatile silicon compound in an oxyhydrogen flame. This results in the production of a finely divided silica. By reaction, the surface can be chemically modified, by reducing the number of silanol groups in order to obtain a hydrophobic silica.

The silica may be present in a quantity ranging from 0.1 to 3% by weight, preferably 0.4–0.8% by weight, relative to the total weight of the composition.

The composition according to the invention is therefore presented in translucent form, i.e., in a non-opaque and non-opalescent form or in a form allowing the passage of light without allowing the forms to be distinguished. Its optical density, determined in a "container" made of quartz and being 10 mm thick, is preferably lower than 1, most preferably of from about 0.1 to 0.6.

The composition according to the invention may comprise, in addition, at least one product in particulate form or in the form of fibres.

This product in particulate form or in the form of fibres may be present in a quantity ranging from 0 to 2% by weight relative to the total weight of the composition, preferably in a quantity ranging from 0.01 to 0.5%.

The product in the form of fibres may be chosen from nylon fibres and aramid fibres.

The expression "aramid fibres" should be understood to mean poly(paraphenyleneterephthalamide) fibres obtained by polymerization of paraphenylenediamine and of terephthallyl chloride. Among the aramid fibres which may be used in the compositions according to the invention, there may be mentioned the fibres known under the tradenames "KEVLAR", in particular "KEVLAR DRY PULP" from the company DUPONT DE NEMOURS, and "ARENKA" from the company ENKA GLANZSTOFF.

The product in the form of particles may be chosen from diamond particles, boron nitride particles, pearl particles and/or pumice particles.

The product in the form of particles may have, preferably, particle sizes ranging from 1 to 100 μm.

The composition according to the invention may comprise, in addition, at least one cosmetically active compound, which may be chosen from vitamins, moisturizers, hardening agents, sunscreens, thickeners and/or raw materials of biological origin. The composition according to the invention may also comprise at least one colorant, or even one inorganic or organic pigment in a small quantity. These additives may be present in a quantity ranging from 0 to 3% by weight relative to the total weight of the composition.

The composition may be presented in the form of a very faintly coloured nail varnish and/or in the form of a nail-care product.

Depending on its final destination, it may comprise the constituents usually present in such compositions.

The subject of the invention is also a method of using pyrogenic silica as a thickening agent for a composition presented in translucent form, especially for a composition that can be applied to the nail.

It has indeed been observed that the composition according to the invention is presented in thickened or even gelled form compared with a composition not comprising pyrogenic silica.

The invention will now be described in greater detail by means of the following examples, which are given solely byway of illustration and in no way limit the invention, and in which the percentages are by weight.

EXAMPLE 1

| Nitrocellulose | 10 g |
| Plasticizer and resin | 15 g |
| Ethyl acetate | 74.5 g |
| Pyrogenic silica (hydrophilic Aerosil 200 from Degussa) | 0.5 g |

The composition obtained is translucent and of suitable texture. It spreads easily on the nails and makes it possible to obtain a suitable uniform and brilliant film.

EXAMPLE 2

| Nitrocellulose | 10 g |
| Plasticizer and resin | 15 g |
| Ethyl acetate | 74.45 g |
| Pyrogenic silica (hydrophobic Aerosil R972 from Degussa) | 0.5 g |
| Diamond powder | 0.05 g |

The composition obtained is translucent and of suitable texture. It contains diamond particles which remain in suspension. It spreads easily on the nails and makes it possible to obtain a suitable uniform film which has a degree of brilliance.

EXAMPLE 3

| Nitrocellulose | 16 g |
| Plasticizer and resin | 15 g |
| Ethyl acetate | 67.9 g |
| Pyrogenic silica | 0.8 g |
| Pearl particles | 0.3 g |

This composition is translucent and makes it possible to obtain a uniform film having good cosmetic properties.

EXAMPLE 4

The direct transmission of light was measured for several compositions comprising pyrogenic silica (Aerosil 100) or bentone.

The composition comprised 10 g. nitrocellulose, 15 g. plasticizer and resin and qsp 100 g. of ethyl acetate.

The optical density of these compositions was measures, in a usual way, utilizing a "container" made of quartz and being 10 mm thick.

The results obtained are:

| Composition | Silica | Bentone | Optical Density |
|---|---|---|---|
| A | — | 3% | 2.250 |
| B | — | 1% | 2.002 |
| C | — | 0.5% | 1.272 |
| D | 3% | — | 0.530 |
| E | 1% | — | 0.253 |
| F | 0.5% | — | 0.158 |
| Control | — | — | 0.026 |

Compositions comprising silica have a low optical density, in comparison with the compositions comprising a usual rheologic agent (bentone).

A visual observation of these compositions gave the following results:

Compositions A, B & C: opaque, very diffusing, and viscous aspect

Compositions D, E & F: translucent, fluid.

What is claimed:

1. A composition for application to a nail comprising at least one film-forming agent, at least one plasticizing agent, at least one solvent, and pyrogenic silica, said composition being translucent and thixotropic, and further comprising at least one cosmetically active compound.

2. A composition according to claim 1, wherein said pyrogenic silica is hydrophilic pyrogenic silica.

3. A composition according to claim 1, wherein said pyrogenic silica is hydrophobic pyrogenic silica.

4. A composition according to claim 1, further comprising at least one product in particulate form, at least one product in the form of fibres, or a mixture of at least one product in particulate form and at least one product in the form of fibers.

5. A composition according to claim 4, wherein said at least one product in particulate form is diamond particles, boron nitride particles, pearl particles, or pumice particles, and wherein said at least one product in the form of fibres is nylon fibres or aramid fibres.

6. A composition according to claim 1, wherein said at least one cosmetically active compound is a moisturizer, a hardening agent, a sunscreen, a vitamin, a thickener, or a raw material of biological origin.

7. A composition according to claim 1, wherein said pyrogenic silica is present in a quantity ranging from 0.1 to 3% by weight relative to the total weight of the composition.

8. A composition according to claim 7, wherein said pyrogenic silica is present in a quantity of 0.4–0.8% by weight relative to the total weight of the composition.

9. A composition according to claim 1 having an optical density lower than 1.

10. A composition according to claim 9 having an optical density ranging from 0.1 to 0.6.

11. A composition according to claim 1, said composition being a nail varnish.

12. A composition according to claim 1, said composition being a nail-care product.

13. A method of thickening a translucent composition comprising preparing a translucent composition containing pyrogenic silica as a thickening agent.

14. A method of thickening a translucent composition comprising adding pyrogenic silica as a thickening agent to a mixture of at least one film-forming agent and at least one solvent, wherein said mixture and said pyrogenic silica form a translucent composition.

15. A composition according to claim 1, wherein said at least one solvent is selected from the group consisting of ethyl alcohol, isopropyl alcohol, butyl alcohol, ethyl acetate, butyl acetate, and ketones.

16. A method of making a composition for application to a nail, comprising the step of combining at least one film-forming agent, at least one plasticizing agent, at least one solvent, and pyrogenic silica, wherein said composition is translucent.

* * * * *